US012575770B2

(12) United States Patent
Sick et al.

(10) Patent No.: US 12,575,770 B2
(45) Date of Patent: Mar. 17, 2026

(54) ELECTRONIC ANKLE MONITOR AND CORRESPONDING PROCESS

(71) Applicant: Dräger Safety AG & Co. KGaA, Lübeck (DE)

(72) Inventors: Michael Sick, Lübeck (DE); Marie-Isabell Mattern-Frühwald, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 265 days.

(21) Appl. No.: 17/389,057

(22) Filed: Jul. 29, 2021

(65) Prior Publication Data

US 2022/0031202 A1 Feb. 3, 2022

(30) Foreign Application Priority Data

Jul. 30, 2020 (DE) ...................... 10 2020 120 111.7

(51) Int. Cl.
*A61B 5/1491* (2006.01)
*A61B 5/00* (2006.01)
*A61B 5/1477* (2006.01)

(52) U.S. Cl.
CPC .......... *A61B 5/1491* (2013.01); *A61B 5/1477* (2013.01); *A61B 5/4845* (2013.01); *A61B 2562/0271* (2013.01); *A61B 2562/029* (2013.01)

(58) Field of Classification Search
None
See application file for complete search history.

(56) References Cited

U.S. PATENT DOCUMENTS

| | | | | |
|---|---|---|---|---|
| 5,944,661 A | * | 8/1999 | Swette | ............... A61B 10/0064 600/362 |
| 2004/0236199 A1 | | 11/2004 | Hawthorne et al. | |
| 2009/0182216 A1 | | 7/2009 | Roushey, III et al. | |
| 2009/0270704 A1 | | 10/2009 | Peyser et al. | |
| 2012/0083710 A1 | * | 4/2012 | Yarden | ................. A61B 5/6802 600/549 |
| 2012/0234078 A1 | * | 9/2012 | Hagl | .................... G01N 27/223 73/29.02 |
| 2013/0006066 A1 | | 1/2013 | Melton | |
| 2016/0000361 A1 | | 1/2016 | Shnaper et al. | |
| 2017/0049397 A1 | * | 2/2017 | Sun | ........................ G01K 7/427 |

(Continued)

FOREIGN PATENT DOCUMENTS

| | | | |
|---|---|---|---|
| DE | 69404472 T2 | 1/1998 | |
| DE | 69404472 T3 | 9/2006 | |

(Continued)

OTHER PUBLICATIONS

Machine translation of WO 2016189053 A1. Retrieved from https://worldwide.espacenet.com/ on Jun. 15, 2023. (Year: 2023).*

(Continued)

*Primary Examiner* — Jacqueline Cheng
*Assistant Examiner* — Samuel C Kim
(74) *Attorney, Agent, or Firm* — McGlew and Tuttle, P.C.

(57) ABSTRACT

An electronic ankle monitor, a process for a control unit of an electronic ankle monitor and a process for detecting alcohol in sweat are provided. The electronic ankle monitor (10) includes an electrochemical sensor (11) and an electrically operated heating element (12) for heating skin (20) in an area around the electrochemical sensor.

20 Claims, 3 Drawing Sheets

(56)                    References Cited

U.S. PATENT DOCUMENTS

| | | | |
|---|---|---|---|
| 2019/0079038 A1* | 3/2019 | Hasegawa ............ | A61B 5/0537 |
| 2019/0110778 A1 | 4/2019 | Heikenfeld et al. | |
| 2019/0183398 A1* | 6/2019 | Heikenfeld .......... | A61B 5/4272 |
| 2019/0374378 A1* | 12/2019 | Weiss ................... | A61B 5/1495 |
| 2021/0137457 A1* | 5/2021 | Matsumoto .......... | A61B 5/4266 |

FOREIGN PATENT DOCUMENTS

| | | | | |
|---|---|---|---|---|
| EP | 3242112 A1 * | 11/2017 | ........... | A61B 5/4266 |
| WO | WO-2016189053 A1 * | 12/2016 | ......... | A61B 5/14521 |

OTHER PUBLICATIONS

Kim et al., 2016, "Noninvasive Alcohol Monitoring Using a Wearable Tattoo Based Iontophoretic Biosensing System,".

* cited by examiner

ELECTRONIC ANKLE MONITOR AND CORRESPONDING PROCESS

CROSS REFERENCE TO RELATED APPLICATIONS

This application claims the benefit of priority under 35 U.S.C. § 119 of German Application 10 2020 120 111.7, filed Jul. 30, 2020, the entire contents of which are incorporated herein by reference.

TECHNICAL FIELD

The present invention pertains to an electronic ankle monitor (ankle shackle or ankle restraint), to a process for a control unit of an electronic ankle monitor, as well as to a process for detecting alcohol in sweat.

TECHNICAL BACKGROUND

One field of application of electrochemical measuring systems is the detection of ethyl alcohol (potable alcohol). This may happen, for example, within the framework of traffic checks, where the electrochemical measuring system is preferably integrated in a breath alcohol measuring device. Another application is, however, the long-term monitoring of alcohol abuse, e.g., within the framework of addiction aid programs or as an obligation imposed as a condition of a probation. On the one hand, a regular measurement over several points of time is required in such scenarios, and, on the other hand, manipulation with the measurement, e.g., by the measurement being carried out on a different person, shall be avoided.

For example, devices that carry out a transdermal measurement of alcohol are known from the US Patent Applications US 2009/0182216 A1 and US 2004/0236199 A1. These may be provided, for example, in the form of an electronic ankle monitor. A detection of alcohol is carried out here from the sweat. However, different test subjects tend to produce sweat at different degrees.

SUMMARY

There consequently is a need for providing an approach for the detection of alcohol, which makes possible, on the one hand, a regular detection over several points in time and, on the other hand, offers a certain protection against manipulations. In addition, the approach should be able to be applied to the largest possible number of persons.

This need is met by the ankle monitor as well as by the processes according to the invention.

Various exemplary embodiments of the present disclosure are based on the discovery that it should be ensured for the reliable measurement of alcohol in human sweat (transcutaneously) that there a sufficient production of sweat even without physical exercise. Studies have shown in this connection that due to physiological differences in the human skin structures, there are persons who sweat less than others. When these persons have consumed alcohol, the measurement of alcohol by means of the transcutaneous detection is possibly less intensive in these persons than in persons who have an enhanced "sweating behavior." Where less sweat is discharged from the skin, the excreted water molecules can carry with them less alcohol and other molecules. The transcutaneous alcohol measurement is possibly limited in these persons based on the small quantity of sweat excreted.

People who sweat less profusely also excrete, in general, less alcohol with the sweat. This alcohol can be detected above the skin by a transcutaneous measuring system, which is configured in exemplary embodiments of the present disclosure, for example, as an ankle monitor (or alternatively as a wristband). Detection by means of a transcutaneous system is rather difficult if the number of alcohol molecules is low.

A research paper by Kim et al., 2016, "Noninvasive Alcohol Monitoring Using a Wearable Tattoo Based Iontophoretic Biosensing System," describes a biosensor system, which is configured in the form of a patch and comprises two systems: first, sweat is produced under the pad by means of the iontophoresis system, and a bio-electrochemical system measures in the second part the alcohol contained in the sweat. The iontophoresis is used here to accelerate the display of alcohol. The time delay between alcohol consumption and the first current values of the transdermal system shall be shortened in this case. The generation of the sweat is carried out in this case by means of the pharmaceutical active ingredient pilocarpine. Pilocarpine belongs to the group of alkaloids. Health hazards for the body and the skin area required are not discussed in the article.

Other types of patches, e.g., heating patches or heated pads (pads) are also known in the literature, but not for the specific, local sweat production in order to obtain, e.g., a reliable result during the transcutaneous measurement of alcohol.

Exemplary embodiments of the present invention create a possibility of stimulating the sweat production specifically at the point at which the transcutaneous detection system is placed, without damaging the skin structures. Exemplary embodiments may be used here to stimulate the skin only as intensely as is needed for a healthy production of sweat, taking into consideration the compatibility with the skin and taking into consideration health aspects.

In order to guarantee a safe and reliable measurement independently from the physiology of the skin, the system being proposed may be configured to produce sweat locally, temporarily and in a defined manner at a location close to the transdermal measuring system. This takes place for health reasons by means of a defined introduction of heat, so that, for example, a temporary heating of the area of the skin, from which an increased quantity of sweat will then be discharged, takes place only when needed (<85% relative humidity over the skin).

Different exemplary embodiments of the present disclosure pertain to an electronic ankle monitor. The electronic ankle monitor comprises an electrochemical sensor. The electronic ankle monitor comprises, furthermore, an electrically operated heating element for heating skin in an area around the electrochemical sensor. Repeated alcohol detection can be made possible by the use of an ankle monitor. The electrochemical sensor is used for the detection of alcohol, while the electrically operated heating element can heat the skin in the area around the electrochemical sensor as needed in order to stimulate the production of sweat. On the one hand, gentle heating of the skin without consequences for the health can be made possible due to the possibility of accurately controlling the electrically operated heating element. On the other hand, the heating may be repeated as frequently as desired within the framework of the energy reserves of the ankle monitor due to the avoidance of the use of drugs.

The electronic ankle monitor comprises in some exemplary embodiments a humidity sensor and a control unit. The control unit is configured, for example, for controlling the electrically operated heating element based on a humidity measured value of the humidity sensor. The control unit may be used in this case to ensure that the heating element is only activated if a stimulation of the sweat production is necessary. In addition, the activation of the heating element may be limited such that the heating element does not remain activated longer than is absolutely necessary.

The electronic ankle monitor may further comprise a temperature sensor. The control unit may further be configured, furthermore, to control the electrically operated heating element on the basis of a temperature measured value of the temperature sensor. The temperature sensor may be used, for example, to measure a temperature on the skin in order to avoid an overheating, which is perceived by the user of the ankle monitor as substantially unpleasant.

The control unit may be configured in this case to process the humidity measured value and/or the temperature measured value in order to actuate the electrically operated heating element selectively on the basis of these measured values. The control unit may be configured, for example, to carry out the process described below.

The electrically operated heating element comprises in some exemplary embodiments a resistance heater. A resistance heater can be placed as a compact unit in the vicinity of the electrochemical sensor.

The electrically operated heating element may be embedded in this case, for example, in a nonwoven. The nonwoven may be configured to be in contact with the skin. A pleasant wearing feeling can be achieved due to the nonwoven, and, in addition, the heat can be transferred via the nonwoven over a larger area to the skin.

In an exemplary implementation, the electrically operated heating element may be arranged, for example, in a ring-shaped manner (in a ring shape). The electrochemical sensor may be configured to carry out an electrochemical measurement based on sweat, which is released from the skin within the ring-shaped heating element. In other words, the sweat can be generated within the ring-shaped heating element, and the electrochemical sensor, as well as optionally the humidity sensor and/or the temperature sensor can carry out measurements within the ring shape formed by the heating element.

In different exemplary embodiments, the electrochemical sensor is a diffusion sensor. As a result, a measurement can be carried out over a longer time period.

The control unit may further be configured, for example, to detect the presence of alcohol in sweat by means of the electrochemical sensor when the sweat is released from the skin. The electronic ankle monitor can thus be used to monitor the presence of alcohol. Consequently, the electronic ankle monitor may be an electronic ankle monitor for monitoring alcohol abuse by means of the electrochemical sensor.

Different exemplary embodiments of the present disclosure also pertain to a process for a control device of an electronic ankle monitor, e.g., for the control device of the above-described ankle monitor. The process comprises the determination of a humidity measured value of a humidity sensor of the electronic ankle monitor. The humidity measured value is based on a humidity of the air in an area around an electrochemical sensor of the ankle monitor. The process further comprises a control of an electrically operated heating element of the electronic ankle monitor based on the humidity measured value. The electrically operated heating element is intended to heat the skin in the area around the electrochemical sensor. A specific control of the electrically operated heating element, with which the heating element is only activated if a stimulation of the sweat production is necessary, can be achieved by the process. In addition, the activation of the heating element can be limited such that the heating element does not remain activated longer than is absolutely necessary.

For example, the electrically operated heating element can be activated if the humidity measured value indicates a humidity in the air that is lower than a threshold value. It is possible not to activate the electrically operated heating element if the humidity measured value indicates a humidity in the air that is higher than the threshold value. As a result, a needless production of additional sweat can be avoided, on the one hand, and, on the other hand, the energy consumption can be lowered.

The electrically operated heating element may remain activated, for example, until an increase in the humidity of the air in the area around the electrochemical sensor can be observed on the basis of the humidity sensor. A certain "sluggishness" of the sweat production can thus also be included in the control of the electrically operated heating element.

The process further comprises in some exemplary embodiments a determination of a temperature measured value of a temperature sensor of the electronic ankle monitor. The temperature measured value may be based on a temperature in the area around the electrochemical sensor. The electrically operated heating element may further be controlled on the basis of the temperature measured value. For example, the temperature on the skin can be taken into consideration in this case in order to avoid skin irritation).

Various exemplary embodiments of the present disclosure pertain to a process for detecting alcohol in sweat. The process comprises a heating of the skin by an electrically operated heating element in an area around an electrochemical sensor. The process further comprises a detection of alcohol in sweat by the electrochemical sensor. The sweat was elicited at least partially by the heating of the skin. On the one hand, gentle heating of the skin without consequences for the health can be made possible in this case by the possibility of accurately controlling the electrically operated heating element.

Some examples of devices and/or processes will be explained in more detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1A:
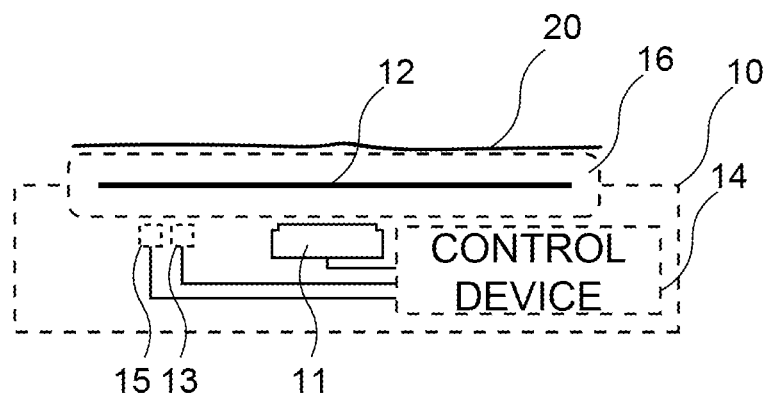
FIG. 1a is a schematic view of an exemplary embodiment of an electronic ankle monitor.

Referring to the drawings, different examples will be described in more detail with reference to the attached figures. The thicknesses of lines, layers and/or areas may be exaggerated for illustration in the Figures.

Further examples may cover modifications, equivalents and alternatives, which fall within the scope of the disclosure. Identical or similar reference numbers refer in the entire description of the figures to identical or similar elements, which can be implemented identically or in a modified form in a comparison with one another, while they provide the same function or a similar function.

Figure 1B:
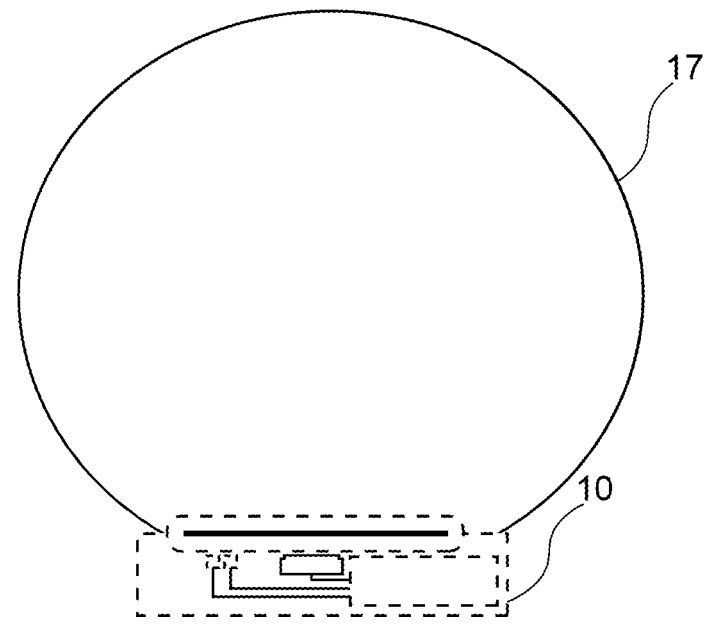
FIG. 1b is a schematic view of another exemplary embodiment of an electronic ankle monitor.

FIGS. 1a and 1b show schematic diagrams of exemplary embodiments of an electronic ankle monitor 10. FIG. 1a shows a sectional view of the electronic ankle monitor, in which the electronic components of the electronic ankle monitor can be seen. FIG. 1b shows a view of the system, where the electronic components can be seen, on the one hand, and where an ankle bracelet 17 for fastening the ankle monitor on the lower leg of a test subject can be seen, on the other hand. While ankle monitors are referred to predominantly in the present disclosure, the same principle, and also the same design may also be used for corresponding wristbands (wrist monitor). In other words, a wristband 10 may also be shown instead of the electronic ankle monitor.

The electronic ankle monitor 10 comprises an electrochemical sensor 11 and an electrically operated heating element 12 for heating skin 20 in an area around the electrochemical sensor. The ankle monitors shown in FIGS. 1a through 1e have additional optional components, which will be described below.

Different exemplary embodiments of the present disclosure pertain to an ankle monitor (or to a wristband) with a heating element, especially with a heating element for the specific, local production of human sweat. This heating element may be used in an ankle monitor to elicit sweat in a specific manner in a test subject, who can subsequently be tested for alcohol by means of the electrochemical sensor. The heating element is preferably embedded here in a skin-friendly contact surface for producing human sweat in a specific manner. The heating element is used, for example, in a combination with a device for detecting ethyl alcohol in human sweat, i.e., with the electrochemical sensor. The detection may take place, for example, at regular intervals, e.g., daily or several times a day, e.g., in order to detect an alcohol abuse by the test subject and optionally to report it. For example, the electronic ankle monitor may be an electronic ankle monitor for monitoring alcohol abuse, e.g., an electronic ankle monitor for monitoring alcohol abuse by means of the electrochemical sensor. In other words, the electronic ankle monitor may be suitable or configured for detecting consumption of alcohol (and consequently also an alcohol abuse) by the test subject with the use of the electrochemical sensor. The electronic ankle monitor is configured in at least some embodiments for the detection of alcohol in the sweat, but not for the determination of the concentration.

The concept described is based on transdermal alcohol measurements, i.e., alcohol measurements via the skin.

Unlike in breath alcohol measuring devices, in which a specifically defined quantity of gas is preferably analyzed in order to be able to generate accurate measurements of the breath alcohol, a different approach, in which the measurement is carried out over a longer time period, is preferably selected within the framework of the present invention. For example, the electrochemical diffusion sensor may be used for this purpose. In other words, the electrochemical sensor may be a diffusion sensor. Contrary to breath alcohol measuring devices, no predefined quantity of gas is analyzed in a diffusion sensor, but the diffusion sensor is exposed to the gas over a longer time period. If the gas, i.e., the evaporated sweat, contains alcohol, the sensor causes the ethyl alcohol (alcohol) to undergo an electrochemical reaction while a current is generated.

Different people produce sweat at different intensities. In order to make it possible to use the approach being presented reliably on different test subjects, the heating element is used within the framework of the present invention in order to guarantee a sufficiently intense sweat production on the skin area on which the measurement is carried out. If necessary, a specific sweat production is elicited by means of heat in order to improve the reliability of the measurement in a skin-friendly manner, because there are people who sweat less profusely and hence, they also release less alcohol (despite a high blood alcohol level) via the sweat. Without the specific sweat production being proposed, these persons cannot otherwise possibly show a positive result with certainty. The approach being proposed is not invasive, and no substances are introduced under the skin.

An electrically operated heating element is used in exemplary embodiments. "Electrically operated" means here that the thermal energy is generated by means of electrical energy. The electrically operated heating element comprises in different exemplary embodiments a resistance heater, i.e., a heating wire, which generates heat while current is flowing through its electrical resistor. The electrically operated heating element 12 is suitable for heating the skin in the area around the electrochemical sensor. The electrically operated heating element 12 is arranged for this purpose in the electronic ankle monitor, for example, such that the electrically operated heating element is arranged adjacent to the skin during the use of the electronic ankle monitor. In addition, the electrically operated heating element 12 may be arranged such that the thermal energy of the heating element heats the skin in the area around the electrochemical sensor. For example, the electrochemical sensor may be arranged at the electrically operated heating element, e.g., in an intermediate space, which is left free by a ring-shaped heating element. For example, the electrically operated heating element 12 may be arranged in the electronic ankle monitor such that the electrically operated heating element is arranged at least partially between the electrochemical sensor and the skin during the use of the electronic ankle monitor. A space, via which the evaporated sweat can diffuse into the electrochemical sensor, may be left free in this case by the electrically operated heating element.

In a preferred embodiment, the electrically operated heating element is embedded, as is shown in FIGS. 1a through 1e, in a nonwoven 16. The nonwoven may be configured to be in contact with the skin. The nonwoven consists, for example, of a material compatible with the skin, for example, a hygienic, medically harmless nonwoven material, which is gentle on the skin and into which the heating element is inserted.

As is shown in FIGS. 1a through 1e, the electrically operated heating element, and hence also the nonwoven, may be ring-shaped. In other words, the electrically operated heating element may be arranged in a ring-shaped manner. Ring-shaped does not (necessarily) mean circular here, but that the electrically operated heating element is led peripherally round a central opening. For example, the nonwoven may be configured as a pad (cushion), and there is a hole in the center of the pad. The pad is coupled with a transcutaneous measuring system. The electrochemical sensor for the transcutaneous measurement of alcohol in the human sweat is arranged above this hole. Different shapes and materials are possible here. For example, the pad may be rectangular, oval or round. The electrochemical sensor may be configured to carry out an electrochemical measurement based on sweat, which is released by the skin within the ring-shaped heating element. The heating element is used for the local heating of the skin area over which the measuring unit for the detection of alcohol in the sweat is arranged. The electrochemical sensor may be arranged for this purpose under the heating element (i.e., on the side of the nonwoven facing away from the skin in FIGS. 1*a*/1*c*) (see FIG. 1*a* and/or FIG. 1*c*), and the gas inlet of the EC (electrochemical) sensor (in the unit) may be arranged within the pad ring, as close as possible to and above the skin. In persons who have a low intensity of sweat production, the skin can be heated in the local area and increased sweat production can thus be forced in a specific manner and without consequences for the health. The size of the heated skin area may correspond approximately to the size of the gas inlet at the measuring system. In order to guarantee a reliable detection of alcohol, a minimum size of skin area, on which the sweat can be detected, may be needed. For example, the central opening of the ring-shaped arrangement may have at least 80% (or at least 100%, at least 120%) of the size of a gas inlet of the electrochemical sensor. The transcutaneous measuring system, which contains an electrochemical alcohol sensor behind the gas inlet opening, then detects the alcohol molecules also discharged in the sweat. The electrochemical alcohol sensor in the measuring system detects the alcohol being discharged selectively and sensitively.

It is also possible in some embodiments to select a completely different approach, in which the electrically operated heating element is a heating grid, and the nonwoven is a heating pad with a grid structure. The heating pad may be, for example, permeable to gases.

The functionality of the electronic ankle monitor is coordinated in at least some exemplary embodiments via a control device 14. This control device may be used, for example, to manage the security aspects of the electronic ankle monitor, e.g., the closed state or the communication with a monitoring station. The control device may be used to control or to operate the electrically operated heating element, i.e., to control a power source of the electrically operated heating element or to provide the power itself. The control of the heater in the nonwoven (i.e., the heating pad) is carried out, for example, by means of software in the control unit/measuring unit. In addition, the control device 14 may be configured to carry out measurements by means of the electrochemical sensor. In other words, the control device may be configured to detect the presence of alcohol in sweat by means of the electrochemical sensor when the sweat is released by the skin. The control unit may be configured to read the current generated during the reaction of alcohol at the electrochemical system. If a flow of current, e.g., a current flow that exceeds a predefined threshold value, is detected, the presence of alcohol can be determined.

In addition to the heating element in the nonwoven, a temperature and/or humidity sensor (T/RH sensor) may additionally be placed directly over the skin area as well. In other words, a T/RH sensor may be located between the skin and the measuring system, and this measures the humidity of the air occurring there directly over the skin. Consequently, the electronic ankle monitor may comprise a humidity sensor 13 and/or a temperature sensor 15. For example, a combined temperature/humidity sensor may be used in some exemplary embodiments.

Both the humidity sensor 13 and the temperature sensor 15 can be used here to determine whether the skin is to be heated, or whether a sufficient humidity and/or sufficient heat are already present. For example, the control device may be configured for controlling the electrically operated heating element based on a humidity measured value of the humidity sensor. In addition, the control device may be configured to control, furthermore, the electrically operated heating element 12 on the basis of a temperature measured value of the temperature sensor 15. The control device may be configured for this purpose to receive the temperature measured value and/or the humidity measured value from the respective sensors. More specific details concerning the control functionality will be explained in connection with the process according to FIG. 2. For example, the control device may be used to carry out the process according to FIG. 2.

In an exemplary application of the concept, the heating pad (ring-shaped, oval, rectangular) is placed between the transdermal measuring system and the skin, so that the gas inlet opening of the sensor is located as close to the skin as possible and the area around this skin area is heated by means of the heating pad comprising nonwoven (unobjectionable for health, skin-friendly) and integrated heater locally and in a targeted manner (when the temperature sensor indicates a temperature of about >28° C.) close to the body, but the humidity of the air at the leg is <85% r. h. Intensified release of sweat takes place in this case locally due to the use of the heater.

The control device 14 may correspond in exemplary embodiments to any desired controller or processor or to a programmable hardware component. For example, the control device 14 may also be embodied as software, which is programmed for a corresponding hardware component. The control device 14 may thus be implemented as programmable hardware with correspondingly adapted software. Any desired processors, such as digital signal processors (DSPs), may be used here. For example, the selection is not limited to a certain type of processor. Any desired processors or even a plurality of processors are conceivable for the implementation of the control device 14.

Figure 1C:
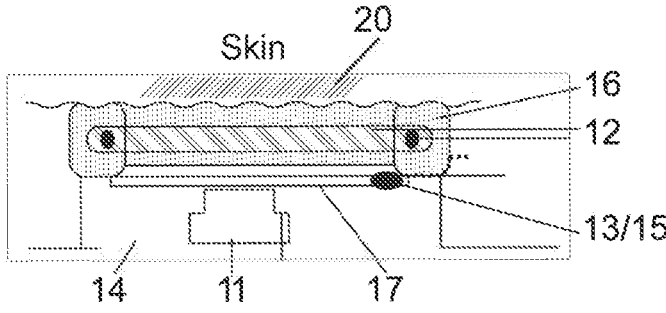
FIG. 1c is a schematic view showing an arrangement with an electrical resistance heater in a nonwoven.
Figure 1D:
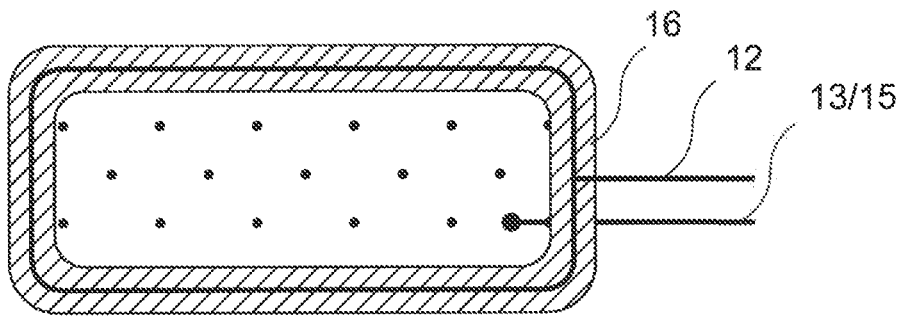
FIG. 1d is another schematic view showing the arrangement with the electrical resistance heater in the nonwoven.
Figure 1E:
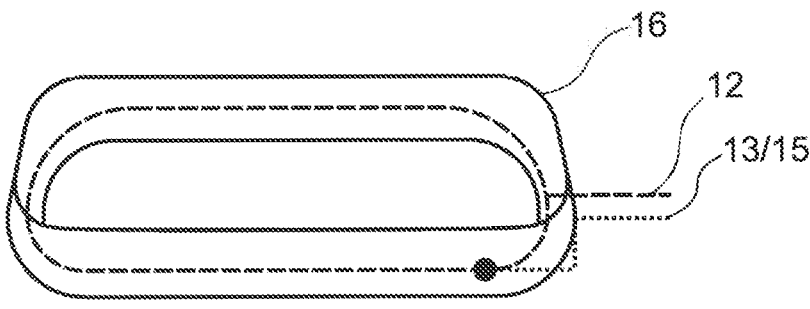
FIG. 1e is another schematic view showing the arrangement with the electrical resistance heater in the nonwoven.

An exemplary implementation of the concept will be shown now in FIGS. 1*c* through 1*e*. The description is focused here on the heating element as well as on the sensors rather than on the ankle monitor or on the wristband per se. FIGS. 1*c* through 1*e* show different perspectives of a schematic drawing of an arrangement with an electrical resistance heater in a nonwoven.

FIG. 1*c* shows a side view of the arrangement as a sectional view. A nonwoven 16, in which the heater (the electrically operated heating element, i.e., e.g., the resistance heater), is embedded, and which is in contact with the skin 20, is shown. The humidity/temperature sensor 13/15 is likewise arranged at the nonwoven 16, on a side of the nonwoven facing away from the skin, and extends into an interior space, which is formed by the nonwoven with the heater. A sensor measuring unit with the electrochemical sensor 11 and with the control unit 14 is likewise arranged on the side of the nonwoven facing away from the skin. FIG. 1*c* shows, furthermore, a perforated orifice/gas inlet for the electrochemical sensor 11.

The arrangement is shown in FIG. 1*d* in a top view. The nonwoven pad 16 (made of a soft, skin-friendly material) has a ring-shaped configuration there, with a hole in the center, into which the humidity/temperature sensor of the respective sensors 13/15 protrudes. The nonwoven pad may have, for example, a round shape, an angular shape or an oval shape with an opening in the center for access to the electrochemical sensor and to the humidity and temperature sensors.

FIG. 1*e* shows a 3D view of the arrangement. It can be seen there that not only is the heating element centered laterally (as is shown in FIG. 1*d*) but is also embedded in a vertically centered manner in the ring-shaped nonwoven.

Figure 2:
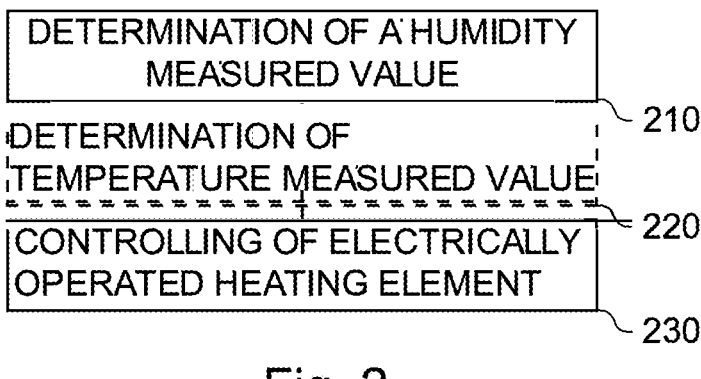
FIG. 2 is a flow chart of an exemplary embodiment of a process for a control device for an electronic ankle monitor.

FIG. 2 shows a flow chart of an exemplary embodiment of a process for a control device for an electronic ankle monitor, e.g., for the control device 14 of the electronic ankle monitor 10 according to FIGS. 1*a* to 1*e*. The process comprises a determination 210 of a humidity measured value of a humidity sensor of the electronic ankle monitor. The humidity sensor is based on the humidity of the air in an area around an electrochemical sensor of the ankle monitor. The process further comprises the controlling 230 of an electrically operated heating element of the electronic ankle monitor on the basis of the humidity measured value. The electrically operated heating element is intended for heating skin in the area around the electrochemical sensor.

While the structural components of the ankle monitor were discussed in connection with FIGS. 1*a* through 1*e*, FIG. 2 pertains to the functionality of the control unit according to an exemplary implementation. The control device is configured, in general, for controlling the electrochemical functionality of the electronic ankle monitor. This includes, for example, the safety aspects, but also the performance of the measurements by means of the electrochemical sensor. The process may correspondingly comprise, furthermore, the performance of an electrochemical measurement by means of the electrochemical sensor. For example, the process may comprise a detection of alcohol in the sweat by means of the electrochemical sensor. The process may comprise, for example, a measurement of a current, which is generated in the electrochemical system. The detection of the alcohol is based on the measured current.

The process comprises the determination 210 of the humidity measured value of the humidity sensor of the electronic ankle monitor. The humidity measured value is based on a humidity of the air in the area around the electrochemical sensor of the ankle monitor, and it may indicate, for example, a relative humidity of the air in the area around the electrochemical sensor. The humidity measured value may be obtained, for example, in the form of a current or of a voltage from the humidity sensor. As an alternative, the humidity measured value can be read or received as a digital value, e.g., if the humidity sensor is a digital sensor.

A temperature measured value is also used in some exemplary embodiments in addition to the humidity measured value. The process may thus also include, furthermore, a determination 220 of a temperature measured value of a temperature sensor of the electronic ankle monitor. Similarly to the humidity measured value, the temperature measured value may be obtained in the form of a current or of a voltage, or else as a digital value. The temperature measured value may be based on a temperature in the area around the electrochemical sensor. The temperature measured value may indicate, for example, the temperature in the area around the electrochemical sensor.

The heating element can be controlled on the basis of the humidity measured value and optionally of the temperature measured value. It can be thus be decided based on the humidity measured value whether an operation of the electrically operated heater is necessary, and the temperature measured value can be used to decide whether the humidity measured value is already meaningful for preventing the temperature on the skin in the area around of the electrochemical sensor from increasing too greatly.

The process further comprises the controlling 230 of the electrically operated heating element of the electronic ankle monitor on the basis of the humidity measured value. For example, the electrically operated heating element can be activated if the humidity measured value indicates a humidity of the air that is lower than a threshold value. The activation of the heating element may comprise in this case the provision of a heating current for the heating element, or a control of a power source for providing the heating current. For example, the electrically operated heating element can be activated if the humidity measured value indicates a relative humidity below 75% (or below 80%, or below 85% or below 90%). In other words, the threshold value may equal 75% (or 80% or 85% or 90%). It is possible not to carry out an activation of the electrically operated heating element if the humidity measured value indicates a relative humidity that is higher than the threshold value. The heater may be switched on additionally temporarily via the control unit, which may be implemented as software (on a microcontroller) at a humidity below 85% r. h. Sweat is produced more intensely when the skin is heated in the area over the skin. People who sweat less profusely can thus nevertheless be tested for alcohol reliably by means of transdermal detection. If a person is already predisposed by nature to produce sweat intensely, the heater would not, for example, be switched on.

In many cases, there is an offset in time between the heating of the skin and the production of sweat. On the one hand, the production of sweat does not cease exactly when the heating element is switched on. The electrically operated heating element can therefore remain activated until an increase can be observed in the humidity of the air in the area of the electrochemical sensor on the basis of the humidity sensor. For example, the electrically operated heating element may remain activated until the humidity of the air has risen by a relative value (for example, +5% percentage points) and/or above a threshold value (e.g., at least 90% or at least 95%). For example, the heater may be switched off again if the humidity of the air reaches 95% relative humidity at the leg, so that battery capacity of the electronic ankle monitor can be saved.

As was mentioned above, the control of the electrically operated heating element may also be made dependent on the temperature measured value. The electrically operated heating element can thus be controlled, furthermore, on the basis of the temperature measured value. For example, an activation of the heater may be indicated if the temperature sensor indicates a near-body temperature of about >28° C., but the relative humidity at the leg is <85% r. h. For example, the measurement of the humidity may be ignored as long as the temperature sensor is below a temperature threshold value, e.g., below 28° C. The temperature measured value may be used during the operation of the heater to limit the output of the electrically operated heating element or to deactivate the electrically operated heating element. For example, the output of the electrically operated heating element may be reduced or the heating element may be deactivated if the temperature in the area around the electrochemical sensor reaches at least 40° C. or at least 45° C.

Figure 3:
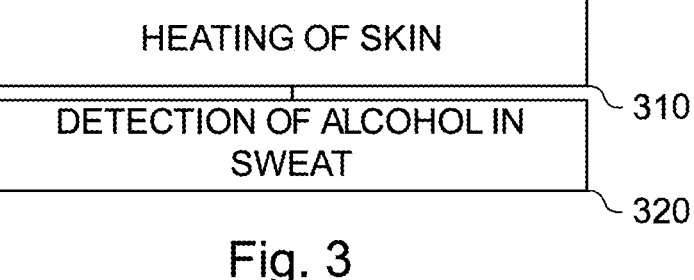
FIG. 3 is a flow chart of an exemplary embodiment of a process for detecting alcohol in sweat.

The general principle of function will be described below once again separately as a process. FIG. 3 shows a flow chart of an exemplary embodiment of a process for detecting alcohol in sweat. The process comprises a heating 310 of skin in an area around of an electrochemical sensor by an electrically operated heating element. The process further comprises a detection 320 of alcohol in sweat by the electrochemical sensor. The sweat was elicited at least partially by the heating of the skin. For example, the process can be carried out by the electronic ankle monitor or by the wristband according to FIGS. 1*a* through 1*e*, e.g., taking into consideration the process according to FIG. 2.

The aspects and features that are described together with one or more of the examples and figures described in detail above may also be combined with one or more of the other examples in order to replace an identical feature of the other example or in order to additionally introduce the feature into the other example.

Furthermore, examples may be or pertain to a computer program with a program code for carrying out one or more of the above processes if the computer program is executed on a computer or processor. Steps, operations or processes of different processes described above may be executed by programed computers or processors. Examples may also cover program memory devices, e.g., digital data storage media, which are machine-, processor- or computer-readable and code machine-executable, processor-executable or computer-executable programs of instructions. The instructions execute some or all of the steps of the above-described processes or cause them to be executed. The program storage devices may comprise or be, e.g., digital memories, magnetic storage media, for example, magnetic disks and magnetic tapes, hard drives or optically readable digital data storage media. Further examples may also cover computers, processors or control units, which are programmed for carrying out the steps of the above-described processes, or (field)-programmable logic arrays ((F)PLAs=(Field) Programmable Logic Arrays) or (field)-programmable gate arrays ((F)PGA=(Field) Programmable Gate Arrays), which are programmed for executing the steps of the above-described processes.

Only basic principles of the disclosure are presented by the description and the drawings. Furthermore, all the examples mentioned here shall expressly serve, in principle, only illustrative purposes in order to support the reader in understanding the basic principles of the disclosure and of the concepts for improving the technique, which have been contributed by the inventor(s). All the statements made herein concerning basic principles, aspects and examples of the disclosure as well as concrete examples thereof comprise equivalents thereof.

A block diagram may represent, for example, a general circuit diagram, which implements the basic principles of the disclosure. Similarly, a flow chart, a process diagram, a state transition diagram, a pseudocode or the like may represent different processes, operations or steps, which are represented, for example, essentially in computer-readable medium and are thus executed by a computer or processor, regardless of whether such a computer or processor is explicitly shown or not. Processes disclosed in the description or in the patent claims may be implemented by a component, which has means for executing each of the respective steps of these processes.

It is apparent that the disclosure of several of the steps, processes, operations or functions disclosed in the description or in the claims shall not be interpreted such that these steps, processes, operations or functions are in a certain sequence, unless this is explicitly or implicitly stated otherwise, e.g., for technical reasons. Therefore, these are not limited by the disclosure of a plurality of steps or functions to a defined sequence, unless these steps or functions are not replaceable for technical reasons. Further, an individual step, function, process or operation may include in some examples a plurality of partial steps, partial functions, partial processes or partial operations and/or is broken down into these partial steps, partial functions, partial processes or partial operations. Such partial steps may be included and be a part of the disclosure of this individual step, unless they are explicitly excluded.

Furthermore, the following claims are hereby included in the detailed description, where each claim may represent a separate example. While each claim may be a separate example in itself, it should be noted that even though a dependent claim may relate in the claims to a defined combination with one or more other claims, other examples may also comprise a combination of the dependent claim with the subject of every other dependent or independent claim. Such combinations are explicitly proposed here unless it is started that a certain combination is not intended. Further, features of a claim shall also be included for each other independent claim, even if this claim is not made directly dependent on the independent claim.

While specific embodiments of the invention have been shown and described in detail to illustrate the application of the principles of the invention, it will be understood that the invention may be embodied otherwise without departing from such principles.

What is claimed is:

1. An electronic monitor comprising:
an electrochemical sensor;
a humidity sensor; and
an electrically operated heating element configured to heat skin of a user in an area around the electrochemical sensor, the electrically operated heating element being in contact with a nonwoven material, the electrically operated heating element comprising an electrically operated heating element surface configured to face in a direction of the skin of the user, wherein at least a portion of the nonwoven material extends along a length of the electrically operated heating element surface, the nonwoven material being configured to be arranged adjacent to the skin of the user, the electrochemical sensor and the humidity sensor being adjacent to the nonwoven material, at least a portion of the electrically operated heating element being configured to be located between the electrochemical sensor and the skin of the user, the electrochemical sensor being located at a spaced location from the electrically operated heating element.

2. The electronic monitor in accordance with claim 1, further comprising:
a control device, wherein the control device is configured to control the electrically operated heating element based on a humidity value measured by the humidity sensor, the nonwoven material completely surrounding the electrically operated heating element.

3. The electronic monitor in accordance with claim 2, further comprising a temperature sensor, wherein the control device is configured to control the electrically operated heating element based on a temperature value measured by the temperature sensor, wherein the portion of the heating element is further configured to be located between the temperature sensor and the skin of the user, the temperature sensor being located at a laterally spaced location from the electrochemical sensor.

4. The electronic monitor in accordance with claim 3, wherein the humidity sensor and the temperature sensor are located on one side of the electrochemical sensor.

5. The electronic monitor in accordance with claim 2, wherein the control device is configured to:

determine the humidity value of the humidity sensor of the electronic monitor, wherein the humidity value is based on a humidity of air in an area around the electrochemical sensor of the electronic monitor.

6. The electronic monitor in accordance with claim 5, wherein:

the control device is configured to activate the electrically operated heating element if the humidity value indicates the humidity of the air is lower than a threshold value, and the control device is configured to not activate the electrically operated heating element if the humidity value indicates the humidity of the air is higher than the threshold value.

7. The electronic monitor in accordance with claim 5, wherein the control device is configured to maintain activation of the electrically operated heating element until an increase can be observed in the humidity of the air in the area around the electrochemical sensor based on the humidity sensor.

8. The electronic monitor in accordance with claim 5, further comprising a temperature sensor, wherein:

the control device is configured to determine a temperature value measured by the temperature sensor;

the temperature value is based on a temperature in the area around the electrochemical sensor;

the temperature sensor is located at a laterally spaced location from the electrochemical sensor and from the humidity sensor;

the humidity sensor is located laterally between the electrochemical sensor and the temperature sensor; and the control device is configured to control the electrically operated heating element, furthermore, based on the temperature value.

9. The electronic monitor in accordance with claim 2, wherein the portion of the heating element is further configured to be located between the humidity sensor and the skin of the user, the humidity sensor being located at a laterally spaced location from the electrochemical sensor.

10. The electronic monitor in accordance with claim 1, wherein the electrically operated heating element comprises a resistance heater, the portion of the nonwoven material being configured to be arranged between the skin of the user and the electrically operated heating element.

11. The electronic monitor in accordance with claim 1, wherein:

the electrically operated heating element is surrounded by the nonwoven material; and the nonwoven material is configured to be in contact with the skin of the user.

12. The electronic monitor in accordance with claim 1, wherein:

the electrically operated heating element is arranged in a ring shape;

the electrochemical sensor is configured to carry out an electrochemical measurement based on sweat which is released within the ring-shaped heating element from the skin.

13. The electronic monitor in accordance with claim 1, wherein the electrochemical sensor is a diffusion sensor.

14. The electronic monitor in accordance with claim 1, further comprising a control device, wherein the control device is configured to detect a presence of alcohol in sweat by means of the electrochemical sensor when the sweat is released from the skin, the control device being located laterally adjacent to the electrochemical sensor.

15. The electronic monitor in accordance with claim 1, wherein the electronic monitor is an electronic monitor for monitoring alcohol abuse by means of the electrochemical sensor.

16. A process for controlling an electronic monitor, the process comprising:

providing an electronic monitor comprising an electrochemical sensor, an electrically operated heating element configured to heat skin of a user in an area around the electrochemical sensor, and a humidity sensor, the electrically operated heating element being in contact with a nonwoven material, the nonwoven material being configured to be arranged adjacent to the skin of the user, wherein a portion of the nonwoven material is configured to extend between the skin of the user and the electrically operated heating element, at least a portion of the electrically operated heating element being configured to be located between the electrochemical sensor and the skin of the user, the electrochemical sensor being located at a spaced location from the electrically operated heating element, the electrochemical sensor and the humidity sensor being arranged adjacent to the nonwoven material;

determining a humidity value measured by the humidity sensor of the electronic monitor, wherein the humidity value is based on a humidity of air in an area around the electrochemical sensor of the electronic monitor; and controlling the electrically operated heating element of the electronic monitor based on the humidity value.

17. The process in accordance with claim 16, wherein the electrically operated heating element is activated if the humidity value indicates the humidity of the air is lower than a threshold value, and wherein an activation of the electrically operated heating element is not carried out if the humidity value indicates the humidity of the air that is higher than the threshold value, the electrically operated heating element comprising an electrically operated heating element surface configured to face in a direction of the skin of the user, wherein the portion of the nonwoven material extends along a length of the electrically operated heating element surface.

18. The process in accordance with claim 16, wherein the electrically operated heating element remains activated until an increase can be observed in the humidity of the air in the area around the electrochemical sensor based on the humidity sensor, the nonwoven material completely surrounding the electrically operated heating element.

19. The process in accordance with claim 16, further comprising determining a temperature value measured by a temperature sensor of the electronic monitor, wherein:

the temperature value is based on a temperature in the area around the electrochemical sensor; and the electrically operated heating element is controlled, furthermore, based on the temperature value.

20. A process for detecting alcohol in sweat, the process comprising the steps of:

measuring a humidity value via a humidity sensor;

heating, based on the humidity value, skin of a user in an area around an electrochemical sensor by an electrically operated heating element, the electrically operated heating element being in contact with a nonwoven material, wherein a portion of the nonwoven material is configured to extend between the skin of the user and the electrically operated heating element, the nonwoven material being configured to be arranged adjacent to the skin of the user, at least a portion of the electrically operated heating element being configured to be located between the electrochemical sensor and the skin of the user, the electrochemical sensor being located at a spaced location from the electrically operated heating element, the electrochemical sensor and the humidity sensor being located adjacent to the nonwoven material; and detecting alcohol in sweat by the electrochemical sensor, wherein the sweat was elicited at least partially by the heating of the skin.

\* \* \* \* \*